United States Patent [19]

Turnbull

[11] Patent Number: 5,250,536
[45] Date of Patent: Oct. 5, 1993

[54] HETEROCYCLIC COMPOUNDS

[75] Inventor: Michael D. Turnbull, Reading, England

[73] Assignee: Imperial Chemical Industries PLC, London, Great Britain

[21] Appl. No.: 853,456

[22] Filed: Mar. 18, 1992

[30] Foreign Application Priority Data

Mar. 28, 1991 [GB] United Kingdom ............... 9106609

[51] Int. Cl.$^5$ ................. C07D 239/38; C07D 239/56; A01N 43/54

[52] U.S. Cl. .................................. 514/269; 514/270; 514/272; 514/274; 514/258; 514/259; 514/260; 544/253; 544/287; 544/285; 544/301; 544/302; 544/303; 544/309; 544/311; 544/312; 544/313; 544/314; 544/319; 544/320; 544/321

[58] Field of Search .............. 544/301, 302, 303, 311, 544/313, 314, 309, 319, 320, 321, 253, 285, 287, 312; 514/269, 272, 274, 270, 258, 259, 260

[56] References Cited

U.S. PATENT DOCUMENTS

| | | | |
|---|---|---|---|
| 3,223,707 | 12/1965 | Brokke | 260/251 |
| 4,423,047 | 12/1983 | Benneche et al. | 424/251 |
| 4,714,706 | 12/1987 | Kisida et al. | 514/345 |
| 4,791,127 | 12/1988 | Kato | 514/369 |

FOREIGN PATENT DOCUMENTS 36839 9/1981 European Pat. Off. .

Primary Examiner—John M. Ford
Attorney, Agent, or Firm—Joel G. Ackerman

[57] ABSTRACT

Compounds of formula (I):

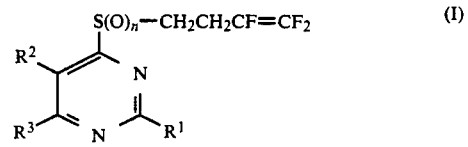

wherein $R^1$, $R^2$ and $R^3$ are independently hydrogen, alkyl, alkenyl, alkynyl, cycloalkyl, alkylcycloalkyl, halogen, haloalkyl, alkoxy, alkenoxy, alkoxyalkyl, haloalkoxy, alkylthio, cyano, nitro, amino, $NR^5R^6$, hydroxy, acylamino, $-CO_2R^4$, $-O(CH_2)_mCO_2R^4$, phenyl, phenoxy, benzyl or benzyloxy, the phenyl group or phenyl moiety of the benzyl group being optionally substituted in the ring; or $R^2$ and $R^3$ when taken together form a 5- or 6-membered ring; m is 1 or 2; $R^4$ and $R^6$ are hydrogen or $C_{1-4}$ alkyl; $R^5$ is $C_{1-4}$ alkyl; n is 0, 1 or 2; are useful as nematicides.

17 Claims, No Drawings

HETEROCYCLIC COMPOUNDS

The present invention relates to novel pyrimidine derivatives having nematicidal activity, to processes for their preparation, to compositions containing them, and to methods for killing or controlling nematode pests using them.

U.S. Pat. No. 3,223,707 describes certain 2-(trifluorobutenylmercapto)-pyrimidine derivatives having nematicidal properties.

According to the present invention there is provided a compound of formula (I) wherein $R^1$, $R^2$ and $R^3$ are independently hydrogen, alkyl, alkenyl, alkynyl, cycloalkyl, alkylcycloalkyl, halogen, haloalkyl, alkoxy, alkenoxy, alkoxyalkyl, haloalkoxy, alkylthio, cyano, nitro, amino, $NR^5R^6$ hydroxy, acylamino, $-CO_2R^4$, $-O(CH_2)_mCO_2R^4$, phenyl, phenoxy, benzyl or benzyloxy, the phenyl group or phenyl moiety of the benzyl group being optionally substituted in the ring; or $R^2$ and $R^3$ when taken together form a 5- or 6-membered ring; m is 1 or 2; $R^4$ and $R^6$ are hydrogen or $C_{1-4}$ alkyl; $R^5$ is $C_{1-4}$ alkyl; n is 0, 1 or 2.

When any of $R^1$, $R^2$ or $R^3$ is an alkyl group it can be straight or branched chain and is preferably $C_{1-4}$ alkyl, in particular ethyl, propyl, isopropyl, n-butyl, iso-butyl, sec-butyl or tertiary butyl.

When any of $R^1$, $R^2$ or $R^3$ is an alkenyl or alkynyl group it can be straight or branched chain and preferably contains up to 6 carbon atoms, for example, allyl or propargyl.

When any of $R^1$, $R^2$ or $R^3$ is a phenyl, phenoxy, benzyl or benzyloxy group, the phenyl moiety may be optionally substituted with halogen, (for example, chlorine or fluorine), cyano, alkyl, haloalkyl, alkoxy or haloalkoxy, the alkyl group being preferably $C_{1-4}$ alkyl and the alkoxy group being preferably $C_{1-6}$ alkyl. Examples of such groups are 2-, 3- or 4-fluorophenyl, 2-, 3- or 4-chlorophenyl, 2,4- or 2,6- difluorophenyl, 2,4- or 2,6-dichlorophenyl, 2-chloro-4-fluorophenyl, 2-chloro-6-fluorophenyl, 2-fluoro-4-chlorophenyl, 2-fluoro-6-chlorophenyl, 2-,3- or 4-methoxyphenyl, 2,4-dimethoxyphenyl, 2-, 3-, or 4-ethoxyphenyl, 2-, 3- or 4-methylphenyl, 2-, 3- or 4-ethylphenyl, 2-, 3- or 4-trifluoromethylphenyl, and the corresponding ring substituted benzyl, phenoxy and benzyloxy groups.

When any of $R^1$, $R^2$ or $R^3$ is a cycloalkyl or alkylcycloalkyl group, it preferably contains from 3 to 7 carbon atoms, for example, cyclopropyl, cyclopentyl, cyclohexyl or methylcyclopropyl.

When any of $R^1$, $R^2$ or $R^3$ is halogen, it is preferably fluorine or chlorine.

When any of $R^1$, $R^2$ or $R^3$ is haloalkyl, the alkyl moiety is preferably $C_{1-4}$ alkyl, for example, trifluoromethyl, trifluoroethyl or pentafluoroethyl.

When any of $R^1$, $R^2$ or $R^3$ is an alkoxy, alkenoxy or alkoxyalkyl group, it can be straight or branched chain and preferably contains up to 6 carbon atoms, for example, methoxy, ethoxy, propoxy, butoxy, butenoxy, methoxymethyl, methoxyethyl or ethoxymethyl.

When any of $R^1$, $R^2$ or $R^3$ is a haloalkoxy group, it can be straight or branched chain and preferably contains up to 6 carbon atoms, for example, trifluoromethoxy, trifluoroethoxy or pentafluoroethoxy.

When any of $R^1$, $R^2$ or $R^3$ is an alkylthio group, the alkyl preferably contains up to 4 carbon atoms. For example, -S-methyl, -S-ethyl, -S-propyl, S-butyl.

When any of $R^1$, $R^2$ or $R^3$ is $NR^5R^6$, it is preferably $NHCH_3N(CH_3)_2$ or $N(C_2H_5)_2$.

When any of $R^1$, $R^2$ or $R^3$ is acylamino, it is preferably $NHCOCH_3$ or $NHCOC_2H_5$.

When any of $R^1$, $R^2$ or $R_3$ is $CO_2R^4$, $R^4$ is preferably hydrogen, methyl or ethyl.

When any of $R^1$, $R^2$ or $R^3$ is $O(CH_2)_mCO_2R^4$, m is preferably 2 and $R^4$ is preferably hydrogen, methyl or ethyl.

When $R^2$ and $R^3$ are taken together to form a 5- or 6-membered ring, it is preferably a carbocylic ring, for example, $-(CH_2)_3-$, $-(CH_2)_4-$ or $-CH=CH-CH=CH-$.

Of particular interest are the compounds of formula (I) where $R^1$ is selected from $C_{1-4}$ alkyl, $C_{1-4}$ haloalkyl, halogen, $C_{1-6}$ alkoxy or hydroxy, $R^2$ is selected from hydrogen, $R^3$ is selected from hydrogen, $C_{1-4}$ alkyl, $C_{1-6}$ alkoxy, hydroxy or halogen and n is 0. Or alternately, the compounds of formula (I) where $R^1$ is phenyl, phenoxy, benzyl or benzyloxy, the phenyl group or phenyl moiety of the benzyl group being optionally substituted, $R^2$ is hydrogen, $R^3$ is selected from hydrogen, $C_{1-4}$ alkyl, $C_{1-6}$ alkoxy, hydroxy or halogen and n is 0.

Examples of the compounds of formula (I) are set out in Table I.

TABLE I

| COMPOUND NO. | $R^1$ | $R^2$ | $R^3$ | n |
|---|---|---|---|---|
| 1 | H | H | H | 0 |
| 2 | H | H | $CF_3$ | 0 |
| 3 | H | H | $CH_3$ | 0 |
| 4 | $CH(CH_3)_2$ | H | $CH_3$ | 0 |
| 5 | $CF_3$ | H | $CF_3$ | 0 |
| 6 | $CH_3$ | H | $CH_2OCH_3$ | 0 |
| 7 | $CH_3$ | $-(CH_2)_3-$ | | 0 |
| 8 | $CH_2CH(CH_3)_2$ | H | $CH_3$ | 0 |
| 9 | $CH_3$ | H | $CH(CH_3)_2$ | 0 |
| 10 | $CH_3$ | H | $CH_3$ | 0 |
| 11 | $C_2H_5$ | H | H | 0 |
| 12 | H | H | $CH(CH_3)_2$ | 0 |
| 13 | $CH_2CH(CH_3)_2$ | H | $CH_3$ | 1 |
| 14 | H | H | $CH(CH_3)_2$ | 1 |
| 15 | H | $-(CH_2)_4-$ | | 0 |
| 16 | $-SCH_3$ | H | H | 0 |
| 17 | H | H | $SCH_3$ | 0 |
| 18 | H | H | $OCH_3$ | 0 |
| 19 | H | H | $OCH_2CF_3$ | 0 |
| 20 | H | H | $O(CH_2)_3CH_3$ | 0 |
| 21 | H | H | $O(CH_2)_3CH_3$ | 2 |
| 22 | H | $CH_3$ | H | 0 |
| 23 | H | $CH(CH_3)_2$ | H | 0 |
| 24 | H | $C_6H_5$ | H | 0 |
| 25 | H | Cl | H | 0 |
| 26 | H | $CH_2OCH_3$ | H | 0 |
| 27 | H | $OCH_2CF_3$ | H | 0 |
| 28 | H | $OCH_2CF_3$ | H | 1 |
| 29 | H | $^cC_3H_5$ | H | 0 |
| 30 | CN | H | H | 0 |
| 31 | CN | H | $CH_3$ | 0 |
| 32 | $^cC_3H_5$ | H | H | 0 |
| 33 | $^cC_3H_5$ | H | Cl | 0 |
| 34 | $C_6H_5$ | H | H | 0 |
| 35 | $CF_3$ | H | H | 1 |
| 36 | $CF_3$ | H | H | 0 |
| 37 | $CF_3$ | H | H | 1 |
| 38 | $OCH_3$ | $CH_3$ | H | 0 |
| 39 | $OCH_3$ | H | $CH_3$ | 0 |
| 40 | $SC_2H_5$ | $CH_3$ | H | 0 |
| 41 | $SC_2H_5$ | H | $CH_3$ | 0 |
| 42 | $CH_2OCH_3$ | H | H | 0 |
| 43 | $CH_2OCH_3$ | $CH_3$ | $CH_3$ | 0 |
| 44 | H | H | $C_6H_5$ | 0 |
| 45 | H | H | $C_6H_5$ | 1 |
| 46 | H | H | $C_6H_5$ | 2 |
| 47 | H | H | $CH_2CH=CH_2$ | 0 |
| 48 | H | H | $C\equiv CH$ | 0 |

TABLE I-continued

| COMPOUND NO. | R¹ | R² | R³ | n |
|---|---|---|---|---|
| 49 | H | H | CN | 0 |
| 50 | H | H | CN | 1 |
| 51 | H |  | —CH=CH—CH=CH— | 0 |
| 52 | OH |  | —CH=CH—CH=CH— | 0 |
| 53 | H |  | —CH=CH—CH=CH— | 1 |
| 54 | H |  | —CH=CH—CH=CH— | 2 |
| 55 | OH |  | —CH=CH—CH=CH— | 1 |

The compounds of formula (I) where n is 0 and $R^1$, $R^2$ and $R^3$ have the meanings defined above are prepared by reacting a correspondingly substituted pyrimidine of formula (II) with 4-bromo-trifluorobut-1-ene in the presence of a base such as a carbonate, for example, potassium carbonate, and an inert solvent, for example acetone. 4-bromo-trifluorobut-1-ene can be obtained by conventional methods or from commercial sources.

Thus, according to a further aspect of the present invention there is provided a process for the preparation of a compound of formula (I) where $R^1$, $R^2$ and $R^3$ have the meanings as defined above and n is 0, which comprises reacting a correspondingly substituted compound of formula (II) with 4-bromo-trifluorobut-1-ene in the presence of a base.

The compounds of formula (I) where any one or more of $R^1$, $R^2$ or $R^3$ is alkoxy can alternatively be prepared by reacting the corresponding hydroxy derivative of formula (I) with an alkylating agent, for example dimethyl sulphate.

Thus, according to a further aspect of the present invention there is provided a process for the preparation of a compound of formula (I) where at least one of $R^1$, $R^2$ or $R^3$ is alkoxy which comprises reacting the corresponding hydroxy derivative of formula (I) with an alkylating agent.

The compound of formula (II) is prepared by reacting a correspondingly substituted pyrimidine of formula (III) with a thiation reagent, for example, phosphorous pentasulphide.

The compounds of formula (I) where n is 1 or 2 and $R^1$, $R^2$ and $R^3$ have the meanings defined above are prepared by oxidising the correspondingly substituted compound of formula (I) where n is 0 using conventional methods, for example, by treatment with a peroxide in an inert organic solvent. Suitable peroxides include organic peroxides such as peroxy carboxylic acids, or their salts, for example, magnesium monoperoxyphthalic acid. Suitable inorganic peroxides include potassium peroxymonosulphate.

Thus, according to a further aspect of the present invention there is provided a process for the preparation of a compound of formula (I) where $R^1$, $R^2$ and $R^3$ have the meanings as defined above and n is 1 or 2, which comprises oxidising the correspondingly substituted compound of formula (I) where n is 0.

The compounds of formula (I) are nematicidal and can be used to control nematodes in crop plants. Therefore, in a further aspect of the invention, there is provided a method for killing or controlling nematodes which comprises applying to the locus of the pests or to a plant susceptible to attack by the pest an effective amount of a compound of formula (I) as defined herein.

The term "controlling" extends to non-lethal effects which result in the prevention of damage to the host plant and the limitation of nematode population increase. These effects may be the result of chemical induced disorientation, immobilisation, or hatch prevention or induction. The chemical treatment may also have deleterious effects on nematode development or reproduction.

The compounds of the invention can be used against both plant-parasitic nematodes and nematodes living freely in the soil. Examples of plant-parasitic nematodes are: ectoparasites, for example *Xiphinema spp., Longidorus spp.* and *Trichodorous spp.*; semi-endoparasites, for example, *Tylenchulus spp.*; migratory endoparasites, for example, *Pratylenchus spp., Radopholus spp.* and *Scutellonema spp.*; sedentary endoparasites, for example, *Heterodera spp., Globodera spp.* and *Meloidogyne spp.*; and stem and leaf endoparasites, for example, *Ditylenchus spp., Aphelenchoides spp.* and *Hirshmaniella spp.*.

The compounds of the invention can also be used in combating a range of insects and acarids. Examples include Lepidoptera, Diptera, Homoptera and Coleoptera (including Diabrotica i.e. corn rootworms).

In order to apply the compound to the locus of the nematode or to a plant susceptible to attack by the nematode, the compound is usually formulated into a composition which includes in addition to the compound of formula (I) suitable inert diluent or carrier materials, and/or surface active agents. Thus in a further aspect of the invention there is provided a nematicidal composition comprising an effective amount of a compound of formula (I) as defined herein and an inert diluent or carrier material and optionally a surface active agent.

The amount of composition generally applied gives a rate of active ingredient from 0.01 to 10 kg per hectare, preferably from 0.1 to 6 kg per hectare.

The compositions can be applied to the soil, plant or seed, in the form of dusting powders, wettable powders, granules (slow or fast release), emulsion or suspension concentrates, liquid solutions, emulsions, seed dressings, fogging/smoke formulations or controlled release compositions, such as microencapsulated granules or suspensions.

Dusting powders are formulated by mixing the active ingredient with one or more finely divided solid carriers and/or diluents, for example natural clays, kaolin, pyrophyllite, bentonite, alumina, montmorillonite, kieselguhr, chalk, diatomaceous earths, calcium phosphates, calcium and magnesium carbonates, sulphur, lime, flours, talc and other organic and inorganic solid carriers.

Granules are formed either by absorbing the active ingredient in a porous granular material for example pumice, attapulgite clays, fuller's earth, kieselguhr, diatomaceous earths, ground corn cobs, and the like, or on to hard core materials such as sands, silicates, mineral carbonates, sulphates, phosphates, or the like. Agents which are commonly used to aid in impregnation, binding or coating the solid carriers include aliphatic and aromatic petroleum solvents, alcohols, polyvinyl acetates, polyvinyl alcohols, ethers, ketones, esters, dextrins, sugars and vegetable oils, with the active ingredient. Other additives may also be included, such as emulsifying agents, wetting agents or dispersing agents.

Microencapsulated formulations (microcapsule suspensions CS) or other controlled release formulations may also be used, particularly for slow release over a period of time, and for seed treatment.

Alternatively the compositions may be in the form of liquid preparations to be used as dips, irrigation additives or sprays, which are generally aqueous dispersions or emulsions of the active ingredient in the presence of one or more known wetting agents, dispersing agents or emulsifying agents (surface active agents). The compositions which are to be used in the form of aqueous dispersions or emulsions are generally supplied in the form of an emulsifiable concentrate (EC) or a suspension concentrate (SC) containing a high proportion of the active ingredient or ingredients. An EC is a homogeneous liquid composition, usually containing the active ingredient dissolved in a substantially non-volatile organic solvent. An SC is a fine particle size dispersion of solid active ingredient in water. To apply the concentrates they are diluted in water and are usually applied by means of a spray to the area to be treated.

Suitable liquid solvents for ECs include methyl ketone, methyl isobutyl ketone, cyclohexanone, xylenes, toluene, chlorobenzene, paraffins, kerosene, white oil, alcohols, (for example, butanol), methylnaphthalene, trimethylbenzene, trichloroethylene, N-methyl-2-pyrrolidone and tetrahydrofurfuryl alcohol (THFA).

Wetting agents, dispersing agents and emulsifying agents may be of the cationic, anionic or non-ionic type. Suitable agents of the cationic type include, for example, quaternary ammonium compounds, for example cetyltrimethyl ammonium bromide. Suitable agents of the anionic type include, for example, soaps, salts of aliphatic monoesters of sulphuric acid, for example sodium lauryl sulphate, salts of sulphonated aromatic compounds, for example sodium dodecylbenzenesulphonate, sodium, calcium or ammonium lignosulphonate, or butylnaphthalene sulphonate, and a mixture of the sodium salts of diisopropyl- and triisopropylnaphthalene sulphonates. Suitable agents of the non-ionic type include, for example, the condensation products of ethylene oxide with fatty alcohols such as oleyl alcohol or cetyl alcohol, or with alkyl phenols such as octyl phenol, nonyl phenol and octyl cresol. Other non-ionic agents are the partial esters derived from long chain fatty acids and hexitol anhydrides, the condensation products of the said partial esters with ethylene oxide, and the lecithins.

These concentrates are often required to withstand storage for prolonged periods and after such storage, to be capable of dilution with water to form aqueous preparations which remain homogeneous for a sufficient time to enable them to be applied by conventional spray equipment. The concentrates may contain 10-85% by weight of the active ingredient or ingredients. When diluted to form aqueous preparations such preparations may contain varying amounts of the active ingredient depending upon the purpose for which they are to be used.

The compounds of formula (I) may also be formulated as powders (dry seed treatment DS or water disperible powder WS) or liquids (flowable concentrate FS, liquid seed treatment LS, or CS) for use in seed treatments. In use the compositions are applied to the nematodes, to the locus of the nematodes, to the habitat of the nematodes, or to growing plants liable to infestation by the nematodes, by any of the known means of applying pesticidal compositions, for example, by dusting, spraying, or incorporation of granules.

The compounds of the invention may be the sole active ingredient of the composition or they may be admixed with one or more additional active ingredients such as nematicides or agents which modify the behaviour of nematodes such as hatching factors, insecticides, synergists, herbicides, fungicides or plant growth regulators where appropriate.

Suitable additional active ingredients for inclusion in admixture with the compounds of the invention may be compounds which will broaden the spectrum of activity of the compounds of the invention or increase their persistence in the location of the pest. They may synergise the activity of the compound of the invention or complement the activity for example by increasing the speed of effect or overcoming repellency. Additionally multi-component mixtures of this type may help to overcome or prevent the development of resistance to individual components.

The particular additional active ingredient included will depend upon the intended utility of the mixture and the type of complementary action required. Examples of suitable insecticides include the following:

a) Pyrethroids such as permethrin, esfenvalerate, deltamethrin, cyhalothrin in particular lambda-cyhalothrin, biphenthrin, fenpropathrin, cyfluthrin, tefluthrin, fish safe pyrethroids for example ethofenprox, natural pyrethrin, tetramethrin, s-bioallethrin, fenfluthrin, prallethrin and 5-benzyl-3-furylmethyl-(E)-(1R,3S)-2,2-dimethyl-3-(2-oxothiolan -3-ylidenemethyl) cyclopropane carboxylate;

b) Organophosphates such as profenofos, sulprofos, methyl parathion, azinphos-methyl, demeton-s-methyl, heptenophos, thiometon, fenamiphos, monocrotophos, profenophos, triazophos, methamidophos, dimethoate, phosphamidon, malathion, chloropyrifos, phosalone, terbufos, fensulfothion, fonofos, phorate, phoxim, pyrimiphos-methyl, pyrimiphos-ethyl, fenitrothion or diazinon;

c) Carbamates (including aryl carbamates) such as pirimicarb, cloethocarb, carbofuran, furathiocarb, ethiofencarb, aldicarb, thiofurox, carbosulfan, bendiocarb, fenobucarb, propoxur or oxamyl;

d) Benzoyl ureas such as triflumuron, or chlorofluazuron;

e) Organic tin compounds such as cyhexatin, fenbutatin oxide, azocyclotin;

f) Macrolides such as avermectins or milbemycins, for example such as abamectin, avermectin, and milbemycin;

g) Hormones and pheromones;

h) Organochlorine compounds such as benzene hexachloride, DDT, chlordane or dieldrin;

i) Amidines, such as chlordimeform or amitraz;

j) Fumigant agents.

In addition to the major chemical classes of insecticide listed above, other insecticides having particular targets may be employed in the mixture if appropriate for the intended utility of the mixture. For instance selective insecticides for particular crops, for example stemborer specific insecticides for use in rice such as cartap or buprofezin can be employed. Alternatively insecticides specific for particular insect species/stages for example ovo-larvicides such as chlofentezine, flubenzimine, hexythiazox and tetradifon, moltilicides such as dicofol or propargite, acaricides such as bromopropylate, chlorobenzilate, or growth regulators such as hydramethylon, cyromazin, methoprene, chlorofluazuron and diflubenzuron may also be included in the compositions.

Examples of suitable synergists for use in the compositions include piperonyl butoxide, sesamax, safroxan and dodecyl imidazole.

Suitable herbicides, fungicides and plant-growth regulators for inclusion in the compositions will depend upon the intended target and the effect required.

An example of a rice selective herbicides which can be included is propanil, an example of a plant growth regulator for use in cotton is "Pix", and examples of fungicides for use in rice include blasticides such as blasticidin-S. The ratio of the compound of the invention to the other active ingredient in the composition will depend upon a number of factors including type of target, effect required from the mixture etc. However in general, the additional active ingredient of the composition will be applied at about the rate as it is usually employed, or at a slightly lower rate if synergism occurs.

The following Examples illustrate the invention. The compounds were identified and characterised by means of the melting points, nuclear magnetic resonance spectroscopy ($^1$H NMR & (CDCl$_3$)), or mass spectroscopy.

EXAMPLE 1

This example illustrates the preparation of Compound No. 1 of Table I.

Step a

Preparation of 4-mercaptopyrimidine

4-Hydroxypyrimidine (1g) and phosphorus pentasulphide (2.32g) were stirred together in 15ml of pyridine and heated to reflux.

After 3 hours at reflux the reaction mixture was allowed to cool, then 30 ml of water was added and the reaction mixture concentrated under reduced pressure. The concentrated mixture was extracted with ethyl acetate (3×30ml) and the combined organic extracts were washed with water, dried over anhydrous MgSO$_4$, filtered and the solvent evaporated under reduced pressure to yield a yellow solid (0.42 g, 36%). The product of this reaction was used in the next preparative step without further purification.

Step b 4-mercaptopyrimidine (0.42 g), 4-bromo-1,1,2-trifluorobut-1-ene (0.71 g) and 0.26g of potassium carbonate were placed together in 10ml of acetone and heated to reflux.

After 1 ½ hours at reflux the reaction mixture was allowed to cool, then filtered to remove insoluble potassium salts. The filtrate was evaporated under reduced pressure to yield a brown oil. The oil was subjected to chromatography using silica eluted with ethyl acetate/hexane (1:4) to yield 0.65 g (79%) of a yellow oil.

Compound No. 1

NMR:2.67–2.85 (m,2H); 3.38 (t,2H); 7.17 (dd,1H); 8.35 (d,1H); 8.95 (s,1H)
M+:220

Compound Nos. 2, 3, 4 and 5 of Table I were prepared by analogy using the preparative route of Example 1.

Compound No. 2

NMR:2.68–2.88 (m,2H); 3.45 (t,2H); 7.50 (s,1H); 9.08 (s,1H)
M+:288

Compound No. 3

NMR:2.43 (s,3H); 2.67–2.85 (m,2H); 3.37 (t,2H); 7.05 (s,1H); 8.82 (s,1H)
M+:234

Compound No. 4

NMR:1.31 (d,6H); 2.40 (s,3H); 2.68–2.86 (m,2H); 3.10 (m,1H); 3.37 (t,2H); 6.84 (s,1H)

Compound No. 5

NMR:2.73–2.91 (m, 2H); 3.49 (t, 2H); 7.63 (s, 1H)
M+:356

EXAMPLE 2

This example illustrates the preparation of Compound No. 6 of Table I. Acetamidine hydrochloride (883 mg) and sodium methoxide (367 mg) were stirred together in 15 ml of ethanol. After ½ hour the reaction was heated to reflux, and methyl 4-methoxy acetoacetate (1 g) was added slowly in 5 ml of ethanol. After 24 hours at reflux the reaction was allowed to cool and filtered to remove insoluble sodium salts. The filtrate was evaporated under reduced pressure to give a yellow oily solid. This was subjected to chromatography using silica and ethyl acetate/hexane (1:4) as the eluent to remove less polar impurities. Further elution with ethanol yielded 800 mg of a yellow solid (75%). The yellow solid was then used to prepare Compound No. 6 of Table I without further purification, using the method (by analogy) described in Example 1 steps a and b. NMR:2.60 (s,3H), 2.68–2.82 (m,2H), 3.35 (t,2H), 3.50 (s,3H), 4.40 (s,2H), 7.10 (s,1H)
M+:278

Compounds Nos. 7, 8, 9 and 10 of Table I were prepared by analogy using the preparative route of Example 2.

Compound No. 7

NMR:2.05–2.20 (m,2H), 2.60 (s,3H), 2.68–2.88 (m,4H), 2.90–3.00 (t,2H), 3.40 (t,2H)
M+: 274.

Compound No. 8

NMR:0.95 (d,6H), 2.15–2.35 (m,1H), 2.40 (s,3H), 2.70 (d,2H), 2.68–2.88 (m,2H), 3.35 (t,2H), 6.85 (s,1H)
M+:290.

Compound No. 9

NMR:1.25 (d,6H), 2.60 (s,3H), 2.68–2.98 (m,3H), 3.35 (t,2H), 6.85 (s,1H)
M+:276.

Compound No. 10

NMR:2.40 (s,3H), 2.60 (s,3H), 2.65–2.85 (m,2H), 3.35 (t,2H), 6.85 (s,1H)
M+:248.

EXAMPLE 3

This example illustrates the preparation of Compound No. 11 of Table I.

Methyl-3-methoxyacrylate (5.8 g) and triethyl-orthopropionate (8.9 g) were placed in a 25 ml autoclave which was purged by pressurising to 30 atmospheres with nitrogen, venting and repeating this process twice more.

Ammonia (4.25 g) was added to the vessel which was heated to 120° C. causing an exotherm to 143° C., the heat was removed and the reaction was left to cool overnight.

The next day the autoclave was initially heated to 80° C., raised at 20° C. per hour to 120° C., kept at this temperature for 12 hours and left to cool. The crude reaction mixture was washed out of the autoclave using ethanol which was subsequently removed by evaporation under reduced pressure. This gave a brown residue. The residue was extracted with diethyl ether (3×50 ml) which on evaporation gave a yellow solid. 1 g of the yellow solid was recrystallised from petroleum ether (80°-100° C. fraction) to give 280 mg of a cream solid.

The cream solid was then used to prepare Compound No. 11 of Table I without further purification using the method (by analogy) described in Example 1, steps a and b.

NMR:1.35 (t,3H), 2.67-2.85 (m,2H), 2.92 (q,2H), 3.28 (t,2H), 6.98 (d,1H), 8.28 (d,1H)

M+:248

EXAMPLE 4

This example illustrates the preparation of Compound No. 12 of Table I.

Sodium metal (2.9 g) and methanol (80 ml) were stirred together, causing the methanol to reflux gently. After 2 hours thiourea (4.8 g) was added.

The reaction was heated gently, to maintain reflux, and then ethyl isobutyryl acetate (10 g) was added dropwise in 20 ml methanol.

After 4 hours the reaction was allowed to cool and the solvents removed under reduced pressure. This residue was poured into 100 ml water and extracted with 50 ml diethylether. The organic layer was discarded. The aqueous layer was acidified with 2M hydrochloric acid and extracted with ethyl acetate (1×100 ml, 1×50 ml). The organic extracts were combined, dried over anhydrous $MgSO_4$, filtered and the solvent evaporated under reduced pressure to yield a yellow solid. The solid was subjected to chromatography using silica and ethyl acetate/hexane (1:1) as the eluent, yielding a white solid.

The white solid (4 g) was suspended in a solution of concentrated ammonia (2.4 ml) in water (65 ml). Raney nickel (8.6 g, 50% dispersion in water) was added and the reaction heated to reflux.

After 4½ hours the reaction was filtered through celite, washing with hot methanol. The filtrate was evaporated under reduced pressure to yield a pale green solid.

The solid was then used to prepare Compound No. 12 of Table I, without further purfication, using the method (by analogy) described in Example 1, steps a and b.

NMR:1.28 (d,6H), 2.68-2.98 (m,3H), 3.40 (t,2H), 7.05 (s,1H), 8.85 (s,1H)

M+:262

Compound No. 15 of Table I was prepared from ethyl 2-cyclohexanone carboxylate, by analogy using the preparative route of Example 4.

Compound No. 15

NMR:1.88 (m,4H), 2.53 (s,2H), 2.65-2.90 (m,4H), 3.40 (t,2H), 8.70 (s,1H)

M+:274

EXAMPLE 5

This example illustrates the preparation of Compound No. 13 of Table I.

Compound No. 8 (1.6 g) was stirred in 20 ml of ethanol. Magnesium monoperoxyphthalic acid hexahydrate (3 g) in 10 ml of water was added dropwise and the reaction heated to 70° C.

After 6 hours the reaction was allowed to cool and poured into 100 ml of saturated sodium bicarbonate solution. This was extracted with ethyl acetate (2×50 ml). The combined organic extracts were washed with saturated sodium bicarbonate solution, dried over anhydrous $MgSO_4$, filtered and the solvent evaporated under reduced pressure, yielding a yellow solid.

The solid was subjected to chromatography using silica and ethyl acetate/hexane (1:4) as the eluent, yielding a yellow oil 750 mg (45%).

NMR:0.95 (d,6H), 2.15-2.35 (m,1H); 2.40-3.95 (m,2H); 2.63 (s,3H); 2.83 (d, 2H), 3.10-3.45 (m, 2H); 7.70 (s, 1H)

M+:306

Compound Nos. 14 and 21 of Table I were prepared by analogy using the preparative method of Example 5.

Compound No. 14

NMR:1.35 (d,6H), 2.45-3.0 (m,2H), 3.09-3.29 (m,2H), 3.35-3.50 (m,1H), 7.90 (s,1H), 9.10 (s,1H)

M+:278

Compound No. 21

NMR:1.00 (t,3H), 1.40-1.55 (m,2H), 1.75-1.85 (m,2H), 2.75-2.95 (m,2H), 3.60 (t,2H), 4.45 (t,2H), 7.40 (t,2H), 8.85 (s,1H)

EXAMPLE 6

This example illustrates the preparation of Compound No. 16 of Table I.

4-Chloro-2-methylthiopyrimidine (2.0 g) and sodium hydrosulphide (1.38 g) were stirred together under nitrogen, in 30 ml of dry dimethylformamide and heated to 100° C.

After 4 hours the reaction mixture was allowed to cool and then poured into 100 ml of water. This was extracted with ethyl acetate (3×30 ml). The combined organic extracts were washed with water, dried over anhydrous $MgSO_4$, filtered and the solvent evaporated under reduced pressure to yield a yellow solid.

The yellow solid was then used to prepare Compound No. 16 of Table I without further purification using the method (by analogy) described in Example 1, step b.

NMR:2.56 (s,3H), 2.67-2.84 (m, 2H), 3.38 (t,2H), 6.82 (d,1H), 8.14 (d,1H)

M+:266

Compound No. 17 was prepared by analogy using the preparative route of Example 6.

NMR:2.53 (s,3H), 2.65-2.82 (m,2H), 3.37 (t,2H), 7.02 (s,1H), 8.70 (s,1H) M+:266

Compound Nos. 51 and 52 were prepared by analogy using the preparative route of Example 6 and Example 1, step b.

Compound No. 51

NMR:2.75-2.95 (m,2H), 3.55 (t, 2H), 7.6 (t, 1H), 7.88 (t? 1H), 7.95 (d, 1H), 8.05 (d, 1H), 9.0 (s, 1H)

Melting point:50.7°-52.0° C.

M+b:270

Compound No. 52

NMR:2.75-2.95 (m, 2H), 3.45 (t, 2H), 7.45 (m, 1H), 7.6 (dd, 1H), 7.88 (dd, 1H), 10.6-10.7 (br, 1H)

Melting point:125.4°-127° C.

EXAMPLE 7

This example illustrates the preparation of Compound No. 18 of Table I.

Sodium metal (322 mg) and methanol (20 ml) were stirred together and heated to maintain reflux. 4,6 Dichloropyrimidine (2 g) was added dropwise in 10 ml of reethanol.

After 21 hours at reflux, sodium methoxide (300 mg) was added in 4 portions over 11 hours while the reaction was maintained at reflux.

The reaction was allowed to cool and the solvent removed under reduced pressure. The residue was poured into 100 ml of $H_2O$ and extracted with ethyl acetate (2×50 ml). The combined organic extracts were dried over anhydrous $MgSO_4$, filtered and the solvent evaporated under reduced pressure yielding a yellow oil.

The yellow oil was then used to prepare Compound No. 18, without further purification, using the methods (by analogy) described in Example 6 and then Example 1, step b.

NMR:2.65–2.85 (m,2H), 3.35 (t,2H), 3.95 (s,3H), 6.60 (s,1H), 8.59 (s,1H)

$M^+$:250.

Compound Nos. 19 and 20 of Table I were prepared by analogy, using the preparative route of Example 7.

Compound No. 19

NMR:2.65–2.85 (m,2H), 3.35 (t,2H), 4.80 (q,2H), 6.73 (s,1H), 8.59 (s,1H)

$M^+$:318

Compound No. 20

NMR:0.95 (t,3H), 1.35–1.55 (m, 2H), 1.68–1.80 (m, 2H), 2.65–2.85 (m,2H), 3.33 (t,2H), 4.30 (t,2H), 6.55 (s,1H), 8.55 (S,1H)

EXAMPLE 8

In order to illustrate the nematicidal properties of the compounds of formula (I), compounds from Table I were tested on root knot nematodes.

Methodology

Test A

Cucumber plants (9 days old, variety 'Telegraph') were soil drenched with a composition of a compound of formula (I) (obtained by diluting 1 part of a solution of the compound in a 1:1 mixture of acetone and ethanol with 99 parts of water containing 0.05% of a wetting agent) at a rate of 40ppm in a drench volume of 10 ml/45 g of soil. The plants were infested with second stage juveniles of the root knot nematode *Meloidogyne incognita* after the solution of the compound had been absorbed by the soil. Nematodes were applied to the roots in a solution of water. The roots of the plants were examined after 9 days to determine the percentage reduction in the number of root knots compated with a control treatment omitting the compound. There were 3 replicates per treatment.

Test B

Tomato plants (6–8 weeks old, variety 'Moneymaker') were planted out into soil infested with second stage juveniles of the root knot nematode Meloidogyne incognita. The soil was drenched with a composition of a compound of formula (I) (obtained by diluting I part of a solution of the compound in a 1:1 mixture of acetone and ethanol with 99 parts of water containing 0.05% of a wetting agent) at a rate of 2.5 or 1.25 ppm in a drench volume of 200 ml/kg of soil. The roots of the plants were examined after 3 weeks to determine the percentage reduction in the number of root knots compared with a control treatment omitting the compound. There were 3 replicates per treatment.

Test C

Tomato plants (6–8 weeks old, variety 'Moneymaker') were transplanted into soil infested with potato cyst nematode (*Globodera rostochiensis*). The soil was drenched with a composition of a compound of formula (I) (obtained by diluting 1 part of a solution of the compound in a 1:1 mixture of acetone and ethanol with 99 parts of water containing 0.05% of a wetting agent) at a rate of 10 or 20 ppm in a drench volume of 266 ml/kg of soil. The cysts were extracted from the soil after 8 weeks by flotation and percentage reduction in the number of cysts compared with a control treatment omitting the compound was determined. There were 5 replicates per treatment.

The results are given in Table II. In the table a blank indicates less than 25% reduction, a hyphen indicates no test carried out at that rate.

TABLE II

| COMPOUND NO. | % ROOT KNOT REDUCTION | | | % CYST REDUCTION | |
|---|---|---|---|---|---|
| | APPLICATION RATE (PPM) | | | | |
| | 40 | 2.5 | 1.25 | 20 | 10 |
| 1 | 94 | 94 | 82 | 100 | 99 |
| 2 | 92 | | | — | — |
| 3 | 94 | 87 | 78 | 94 | — |
| 4 | 97 | | | — | — |
| 5 | 91 | — | — | — | — |
| 6 | 76 | | | — | — |
| 9 | 95 | | | — | — |
| 10 | 95 | | | — | — |
| 11 | 100 | 89 | 79 | — | — |
| 12 | 91 | — | — | — | — |
| 13 | 100 | | | — | — |
| 14 | 100 | | | — | — |
| 16 | 98 | 26 | | — | — |
| 17 | 77 | | | — | — |
| 19 | 94 | 90 | 94 | — | — |
| 20 | 87 | | | — | — |
| 21 | 99 | — | — | — | — |
| 51 | 94 | | | — | — |
| 52 | 95 | | | 90 | — |

The compounds of formula (I) display nematicidal activity against different types of nematodes including the cyst nematode. A further advantage is that the compounds are not phytotoxic to the target plant. Very little phytotoxicity was observed in the above tests. This is a particularly desirable feature when treating young plants and seeds.

The following examples demonstrate formulations suitable for applying the compounds of the present invention. The amount of ingredient is expressed in parts by weight or grams per liter as indicated. A * indicates a trademark.

EXAMPLE 9

This example demonstrates granules suitable for soil application. The granules can be made be standard techniques such as impregnation, coating, extrusion or agglomeration.

| | % w/w |
|---|---|
| Impregnated granule: Active ingredient | 5 |
| Wood Rosin | 2.5 |
| Gypsum granules (20–40 mesh) | 92.5 |
| Coated granule: Active ingredient | 0.5 |
| 'Solvesso'* 200 | 0.4 |
| Calcium carbonate granules (30–60 mesh) | 99.1 |
| Slow release granule: Active ingredient | 10 |
| Polyvinylacetate/vinyl chloride copolymer latex | 5 |
| Attapulgus granules | 85 |

EXAMPLE 10

This example demonstrates formulations for use as a spray. The compounds can be formulated as wettable powders, water dispersible granules, suspension concentrates, emulsifiable concentrates, emulsions or microcapsule suspensions for application diluted in water.

| | | g/l |
|---|---|---|
| Emulsifiable concentrate: | Active ingredient | 250 |
| | Calcium dodecylbenzene sulphonate | 50 |
| | Nonyl phenol ethoxylate | 50 |
| | Alkylbenzene solvent | to 1 liter |

| | | % w/w |
|---|---|---|
| Wettable powder: | Liquid active ingredient | 40 |
| | lignosulphonate dispersant | 5 |
| | silica | 25 |
| | sodium lauryl sulphate | 3 |
| | china clay (kaolin) | 27 |
| Microcapsule suspension: | Liquid active ingredient | 250 |
| | toluene diisocyanate polymethylene polyphenyl isocyanate | 10 |
| | | 20 |
| | nonyl phenol ethoxylate | 6 |
| | lignosulphonate dispersant | 15 |
| | xanthan gum | 1 |
| | bentonite | 10 |
| | biocide 'Proxel'* | 0.1 |
| | sodium carbonate | 5 |
| | water | to 1 liter |

The microcapsule suspensions can be used as a spray, soil drench or as an intermediate to prepare slow release granules for application to the soil.

| | | g/l |
|---|---|---|
| Suspension concentrate: | Solid active ingredient | 400 |
| | lignosulphonate dispersant | 50 |
| | sodium lauryl sulphate | 30 |
| | xanthan gum | 1 |
| | biocide 'Proxel'* | 0.1 |
| | bentonite | 10 |
| | water | to 1 liter |

EXAMPLE 11

This example demonstrates formulations suitable for use as seed treatments in conventional application machinery.

| | | % w/w |
|---|---|---|
| Dry seed treatment: | Active ingredient | 20 |
| | dodecyl benzene | 3 |

-continued

| | | % w/w |
|---|---|---|
| | Rubine Toner (dyestuff) | 2.7 |
| | Talc | 53.3 |
| | Silica | to 100% |

The suspension concentrate and microcapsule suspension of Example 4 can be used as flowable concentrates for seed treatment.

EXAMPLE 12

This example demonstrates the formulation of the compounds for electrostatic spraying.

| | g/l |
|---|---|
| Active ingredient | 200 |
| N-methylpyrollidone | 50 |
| Soyabean oil | 120 |
| 'Solvesso'* 200 | to 1 liter |

CHEMICAL FORMULAE (corresponding to formulae numbers in the description)

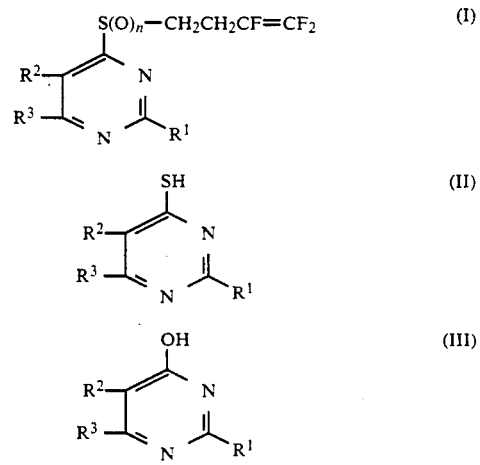

I claim:

1. A compound of formula (I):

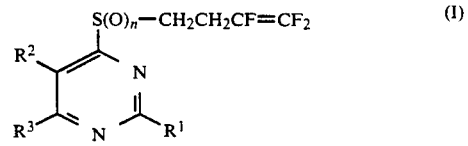

wherein $R^1$, $R^2$ and $R^3$ are independently hydrogen, $C_1$–$C_4$ alkyl, $C_2$–$C_6$ alkenyl, $C_2$–$C_6$ alkynyl, $C_3$–$C_6$ cycloalkyl, $C_3$–$C_7$ alkylcycloalkyl, halogen, $C_1$–$C_4$ haloalkyl, $C_1$–$C_4$ alkoxy, alkenoxy containing up to 6 carbon atoms, alkoxyalkyl containing up to 6 carbon atoms, haloalkoxy containing up to 6 carbon atoms, $C_1$–$C_4$ alkylthio, cyano, nitro, amino, $NR^5R^6$, hydroxy, $NHCOCH_3$, $NHCOC_2H_5$, —$CO_2R^4$, —$O(CH_2)_mCO_2R^4$, phenyl, phenoxy, benzyl or benzyloxy, the phenyl group or phenyl moiety of the benzyl group being optionally substituted in the ring with halogen, cyano, $C_1$–$C_4$ alkyl, $C_1$–$C_4$ haloalkyl, $C_1$–$C_4$ alkoxy, $C_1$-$C_6$ haloalkoxy; or $R^2$ and $R^3$ when taken together form —$(CH_2)_3$—, —$(CH_2)_4$— or —CH=CH—CH=CH—; m is 1 or 2; $R^4$ and $R^6$ are hydrogen or $C_{1-4}$ alkyl; $R^5$ is $C_{1-4}$ alkyl; n is 0, 1 or 2.

2. A compound according to claim 1 wherein $R^1$ and/or $R^3$ is independently hydrogen, alkyl, alkenyl, alkynyl, halogen, haloalkyl, alkoxy, haloalkoxy, alkylthio or hydroxy.

3. A compound according to claim 1 wherein $R^1$ and/or $R^3$ is independently hydrogen, $C_{1-4}$ alkyl, $C_{1-4}$ haloalkyl, $C_{1-6}$ alkoxy, $C_{1-6}$ haloalkoxy, chlorine or fluorine.

4. A compound according to claim 1 wherein $R^1$ and/or $R^3$ are independently phenyl, phenoxy, benzyl or benzyloxy, the phenyl group or phenyl moiety of the benzyl group being optionally substituted in the ring.

5. A compound according to claim 4 wherein the phenyl, phenoxy, benzyl or benzyloxy group is substituted with one or more of halogen, cyano, alkyl, haloalkyl, alkoxy or haloalkoxy.

6. A compound according to claim 1 wherein $R^2$ is hydrogen.

7. A compound according to claim 1 wherein $R^2$ is $C_{1-4}$ alkyl, $C_{1-4}$ haloalkyl or halogen.

8. A compound according to claim 1 wherein the $R^2$ and $R^3$ taken together form a 5- or 6-membered carbocylic ring.

9. A compound according to claim 1 wherein $R^1$, $R^2$ and $R^3$ are all hydrogen.

10. A compound according to claim 1 wherein n is 0.
11. A compound according to claim 1 wherein n is 1.
12. A compound according to claim 1 wherein n is 2.
13. A compound according to claim 1 wherein $R^1$ is hydrogen, $C_{1-4}$ alkyl, $C_{1-4}$ haloalkyl, halogen, $C_{1-6}$ alkoxy, $C_{1-6}$ haloalkoxy, $C^{1-4}$ alkylthio or hydroxy, $R^2$ is hydrogen and $R^3$ is hydrogen, $C_{1-4}$ alkyl, $C_{1-4}$ haloalkyl, halogen, $C_{1-6}$ alkoxy, $C_{1-6}$ haloalkoxy, $C^{1-4}$ alkylthio or hydroxy and n is 0.

14. A compound according to claim 1 wherein $R^1$ is phenyl, phenoxy, benzyl or benzyloxy, the phenyl group or phenyl moiety of the benzyl group being optionally substituted, $R^2$ is hydrogen, and $R^3$ is hydrogen, $C_{1-4}$ alkyl, $C_{1-6}$ alkoxy, hydroxy or halogen and n is 0.

15. A compound of formula (I):

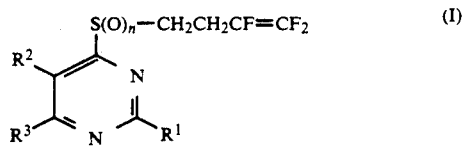

wherein $R^1$, $R^2$ and $R^3$ are independently hydrogen, $C_1$-$C_4$ alkyl, $C_2$-$C_6$ alkenyl, $C_2$-$C_6$ alkynyl, phenyl optionally substituted with halogen, cyano, $C_1$-$C_4$ alkyl, $C_1$-$C_4$ haloalkyl, $C_1$-$C_4$ alkoxy, $C_1$-$C_6$ haloalkoxy, $C_3$-$C_7$ cycloalkyl, $C_3$-$C_7$ alkylcycloalkyl, halogen, $C_1$-$C_4$ haloalkyl, $C_1$-$C_4$ alkoxy, $C_1$-$C_4$ alkylthio, cyano or hydroxy; and n is 0, 1 or 2.

16. A nematicidal composition comprising an effective amount of a compound of formula (I) as defined in any of claims 1-5 or 7 and an inert diluent or carrier material and optionally a surface active agent.

17. A method for killing or controlling nematode pests which comprises applying to the locus of the pests or to a plant susceptible to attack by the pest an effective amount of a compound of formula (I) as defined in any of claims 1-5 or 7.

* * * * *